(12) United States Patent
Nomura

(10) Patent No.: US 6,593,260 B2
(45) Date of Patent: Jul. 15, 2003

(54) ANTIBACTERIAL PROPERTY IMPARTING GLASS COMPOSITION

(75) Inventor: Makio Nomura, Nagoya (JP)

(73) Assignee: Ishizuka Garasu Kabushiki Kaisha, Aichi (JP)

(*) Notice: Subject to any disclaimer, the term of this patent is extended or adjusted under 35 U.S.C. 154(b) by 205 days.

(21) Appl. No.: 09/742,437

(22) Filed: Dec. 22, 2000

(65) Prior Publication Data

US 2001/0023156 A1 Sep. 20, 2001

(30) Foreign Application Priority Data

Dec. 28, 1999 (JP) .......................................... 11-375579
Sep. 26, 2000 (JP) ....................................... 2000-292964

(51) Int. Cl.⁷ ............................. C03C 3/17; C03C 13/00
(52) U.S. Cl. .............................. 501/48; 501/47; 501/35
(58) Field of Search ............................. 501/48, 47, 35

(56) References Cited

U.S. PATENT DOCUMENTS 6,410,633 B1 * 6/2002 Hikata et al. ............... 524/405

FOREIGN PATENT DOCUMENTS

| JP | 4-338129 | * | 11/1992 |
| JP | 6-287811 | * | 10/1994 |
| JP | 9-56530 | * | 8/1995 |
| JP | 7-300339 | | 11/1995 |
| JP | 9-105222 | * | 4/1997 |
| JP | 2000-191339 | * | 7/2000 |
| JP | 2000-327364 | * | 11/2000 |
| JP | 2001-139832 | * | 5/2001 |
| JP | 2002-87842 | * | 3/2002 |

* cited by examiner

*Primary Examiner*—Karl Group
(74) *Attorney, Agent, or Firm*—Townsend & Banta

(57) ABSTRACT

An antibacterial property imparting glass composition is provided, which may be fixed in a form of, for example, a particle on the surface of a fiber substrate and/or dispersed and complexed in the fiber substrate. Such an antibacterial property imparting glass composition comprises 0.1 to 5.0% by weight of $Ag_2O$ in a composition containing 45–67 mol % of $P_2O_5$, 5 to 20 mol % of $Al_2O_3$, 1 to 40 mol % of 1 or 2 or more selected from MgO, CaO and ZnO, and 20 mol % or less of $B_2O_3$. An antibacterial fiber containing such an antibacterial property imparting glass composition at a ratio of, for example, 0.1 to 5.0% by weight shows high water resistance, acid resistance, alkali resistance and detergent resistance in antibacterial property.

3 Claims, 11 Drawing Sheets

ANTIBACTERIAL PROPERTY IMPARTING GLASS COMPOSITION

RELATED APPLICATION

This application claims the priority of Japanese Patent Applications No. 11-375579 filed on Dec. 28, 1999, and No. 2000-292964 filed on Sep. 26, 2000, which are incorporated herein by reference.

FIELD OF THE INVENTION

The present invention relates to an antibacterial property imparting glass composition, an antibacterial fiber, an antibacterial twisted yarn and an antibacterial cloth.

BACKGROUND OF THE INVENTION

In four seasons in our country (Japan), there is the circumstance in which bacteria tend to grow. In particular, under a high temperature and high humidity in the summer season and the rainy season, the growth of microorganism becomes active. For that reason, people is suffering from sudamen, athlete's foot, bedsore and uncomfortable smell in many cases. With diversification of a life style, fiber products having microorganism controlling ability which inhibit or sterilize harmful microorganism growing in clothes, that is, antibacterial fiber products treated with so-called antibacterial and anti-smell processing have spread.

For example, there is an antibacterial fiber product complexed with an inorganic antibacterial agent, for example, zirconium phosphate loaded with silver, silver zeolite, soluble glass or the like. In particular, a soluble glass refers collectively to glasses having the adjusted composition from a viewpoint of the physical and chemical properties of a glass so that the glass has the controlled dissolving rate, and soluble glasses containing a silver, copper or zinc compound having antibacterial property are known as a glass which can dissolve out the above silver, copper or zinc ion at the predetermined rate for a few hours to a few years. Dissolved out silver, copper and zinc ions are adsorbed on a cell membrane of bacteria or microorganism, or concentrated in the cells, which inhibits the growth of bacteria or microorganism and exerts the antibacterial action by so-called oligodynamic action.

OBJECTS OF THE INVENTION

Since antibacterial fibers containing the above inorganic antibacterial agent such as a soluble glass and the like have many chances to contact with water and a detergent by washing or the like, the antibacterial effects can not be retained and there is also a problem that the antibacterial effects are lowered by post-processing (processing after complexed with an antibacterial agent, for example, acid treatment, alkali treatment and the like) such as fiber staining. For that reason, a large amount of an antibacterial agent is necessary to be added and, when the amount to be added is increased, not only it becomes high cost but also there arises easily a problem of discoloration due to silver or the like contained in an inorganic antibacterial agent and, thus, it is not preferable from a viewpoint of appearances.

An object of the present invention is to provide an antibacterial property imparting glass composition which can, at a small amount, impart high antibacterial durability to water, a detergent, post-processing with staining or the like, an antibacterial fiber using the same, an antibacterial twisted yarn and an antibacterial cloth.

SUMMARY OF THE INVENTION

In order to solve the above object, an antibacterial property imparting glass composition of the present invention is characterized in that $Ag_2O$ is contained, at 0.1–5.0% by weight, in a glass composition containing 45–67 mol % of $P_2O_5$, 5–20 mol % of $Al_2O_3$, and 1–40 mol % of 1 or 2 or more selected from MgO, CaO and ZnO. In addition, an antibacterial fiber of the present invention is characterized in that the antibacterial property imparting glass composition is complexed with a synthetic fiber or a natural fiber.

DETAILED DESCRIPTION OF THE INVENTION

Figure 1A:
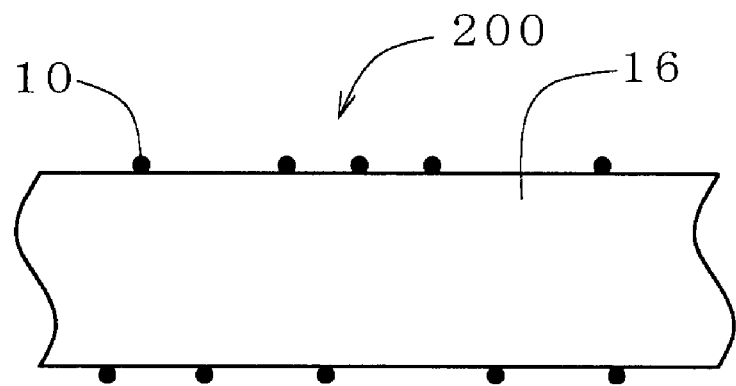
FIGS. 1A and 1B are views schematically showing an example of the morphology of an antibacterial fiber of the present invention.

The glass composition having the above essential features is generally a soluble glass and the Ag component contained in a glass composition (soluble glass) is dissolved out from a glass composition for imparting antibacterial property containing such the soluble glass at the predetermined rate for an arbitrary period of time and, whereby, the antibacterial fiber becomes to have high antibacterial property due to the Ag component. In the antibacterial property imparting glass composition of the present invention, since 5–20 mol % of $Al_2O_3$, and 1–40 mol % of 1 or 2 or more selected from MgO, CaO and ZnO (hereinafter, this is also referred to as water resistance imparting component) are contained as a component for improving acid-resistance, alkali-resistance and water-resistance, the antibacterial property imparting glass composition exerts, at a small amount, the antibacterial effects on a fiber material which should be given the antibacterial property and at the same time becomes to impart acid-resistance, alkali-resistance and water-resistance. For example, a fiber material complexed with the antibacterial property imparting glass composition exerts high antibacterial durability to post-processing (processing performed, for example, by an acid or an alkali after complexed with an antibacterial agent) such as staining.

Further, since the content of $Al_2O_3$ in the glass composition is 5–20 mol % and the content of the water-resistance imparting component in the glass composition is 1–40 mol %, the composition can sufficiently impart detergent-resistance to a subject material such as a fiber material and the like and, in particular, when a fiber product which is constituted by the antibacterial fiber is washed, the antibacterial property sustaining effects are exerted.

As the post-processing of a fiber material, there can be exemplified weight loss processing (denier reduction (caustic reduction)) with an acid or an alkali (for example, soaking treatment in a 4% aqueous solution of sodium hydroxide at 98° C. for 40 minutes dipping, as alkali reduction), staining treatment (for example, with an acid having hydrogen ion concentration of 4 or less) and the like. An antibacterial fiber complexed with an antibacterial property imparting glass composition of the present invention shows high antibacterial sustaining effect to such the post-processing and also shows high antibacterial property even after post-processing.

In addition, $Al_2O_3$ is a component for enhancing water-resistance, detergent-resistance, in particular, acid-resistance and alkali-resistance. When the content of $Al_2O_3$ in a glass composition is less than 5 mol %, the effects of improving water-resistance, detergent-resistance, acid-resistance and alkali-resistance become insufficient in some cases. In addition, the content of $Al_2O_3$ exceeds 20 mol %, vitrification of a soluble glass becomes difficult in some cases. The content of $Al_2O_3$ is preferably 7–18 mol %.

In addition, when the content of the aforementioned water-resistance imparting component in a glass composition is less than 1 mol %, sufficient water-resistance of a glass composition (soluble glass) is not obtained and, a dissolution rate of a glass is too large, antibacterial sustaining effect of an antibacterial fiber to water is decreased in some cases. When the content of a water-resistance imparting component exceeds 40 mol %, a dissolution rate of a soluble glass to water becomes small, and the antibacterial effects to a subject material of a fiber or the like to which antibacterial property is to be imparted by addition of a small amount of an antibacterial property imparting glass composition become unexpected in some cases and, conversely, a dissolution rate becomes large to a detergent and the antibacterial durability of a fiber or the like to a detergent becomes unexpected in some cases and, additionally, the antibacterial sustaining effect to a detergent is lowered in some cases. The content of a water-resistance imparting component in a glass composition is preferably 4–35 mol %, more preferably 7–22 mol %.

Next, critical meanings (limit effect) of each component contained in an antibacterial property imparting glass composition of the present invention will be explained below.

$P_2O_5$ is a main component for glass formation in a glass composition (soluble glass). When the content of $P_2O_5$ in a glass composition is less than 45 mol %, vitrification of a soluble glass becomes difficult in some cases. In addition, when the content of $P_2O_5$ exceeds 67 mol %, water-resistance of a glass composition is lowered in some cases. The content of $P_2O_5$ is preferably 45–65 mol %, more preferably 50–60 mol %.

$B_2O_3$ can be contained in the aforementioned glass composition in a range of 20 mol % or less (lower limit is 0.1 mol %). $B_2O_3$ is a component for glass formation next to $P_2O_5$ in a soluble glass. When the content of $B_2O_3$ exceeds 20 mol %, vitrification of a soluble glass becomes difficult in some cases. The content of $B_2O_3$ is preferably 0.1–18 mol %.

In the present invention, $Ag_2O$ is contained in such the glass composition at an amount of 0.1–5.0% by weight and this Ag component is a main component for manifesting the antibacterial action. When the content of $Ag_2O$ in a glass composition is less than 0.1% by weight, the antibacterial effect by addition of the antibacterial property imparting glass composition to a fiber at a small amount can not be obtained in some cases. On the other hand, when the content of $Ag_2O$ exceeds 5.0% by weight, discoloration is produced in the antibacterial fiber in some cases. The content of $Ag_2O$ in a glass composition is preferably 0.1–3.5% by weight, more preferably 0.5–3.5% by weight.

Next, 1 or 2 or more selected from $Li_2O$, $Na_2O$ and $K_2O$ (hereinafter, also referred to as vitrification promoting component) can be contained in the above glass composition in a range of 15 mol % or less (lower limit is 0.1 mol %). The aforementioned vitrification promoting component makes vitrification of a glass composition (soluble glass) easy but, when the content exceeds 15 mol %, a dissolution rate of a glass composition (soluble glass) to water becomes large and, in an antibacterial fiber complexed with the antibacterial property imparting glass composition, the antibacterial sustaining effect to water, detergent, acid and alkali is lowered in some cases. The content of a vitrification promoting component in a glass composition is preferably 0.1–13 mol %.

The antibacterial property imparting glass composition having such the essential features is suitably finely-ground into the particle form to complex with a synthetic fiber or a natural fiber. In such the case, an average particle diameter can be 0.05–55 μm. When an average diameter is less than 0.05 μm, preparation of a particle becomes difficult in some cases and, additionally since, when complexed with the above fiber, deviation is produced and complexation can not be performed uniformly in some cases, the antibacterial property imparting effect is lowered and the performance of a fiber itself is lowered, in particular, at the deviation region in some cases. In addition, when an average particle diameter exceeds 55 μm, the property of a fiber itself is lowered and appearances of the resulting antibacterial fiber are deteriorated in some cases. An average particle diameter is preferably 0.1–55 μm, more preferably 0.5–55 μm.

An average particle diameter can be measured using laser diffraction type granulometer. In this case, since a great difference is not produced between the diffraction behavior of incident laser light due to an aggregated particle and the diffraction behavior due to isolated primary particle, whether measured particle diameter is a particle diameter of the existing single primary particle or a particle diameter of aggregated secondary particle is not discriminated. Therefore, an average particle diameter measured by the method is a value which reflects an average particle diameter of a secondary particle including an isolated and not aggregated primary particle in a broad sense.

When an antibacterial fiber of the present invention is obtained by the aforementioned antibacterial property imparting glass composition, an antibacterial property imparting glass composition is suitably complexed with a synthetic fiber or a natural fiber at a ratio of 0.1–5.0% by weight. In an antibacterial fiber of the present invention, even when an amount of an antibacterial property imparting glass composition to be added is small (low complexation), sufficient water-resistance, detergent-resistance, acid-resistance and alkali-resistance can be exerted for the aforementioned reasons. When a complexed amount is less than 0.1% by weight, sustained antibacterial property of the antibacterial fiber to water, detergent, acid and alkali can not be obtained in some cases. When the amount exceeds 5.0% by weight, the nature originally harbored by a fibrous polymer is lowered and appearances of an antibacterial fiber are deteriorated in some cases and, additionally, a problem of high cost arises in some cases. The complexed amount is preferably 0.1–2.5% by weight.

When an antibacterial property imparting glass composition is complexed with a fiber, regarding a natural fiber, complexation is possible by combining 1 or 2 or more of the following aspects:
(1) fixation of a particle at the surface at a fiber stage,
(2) fixation of a particle at a twisted yarn or final fiber stage.

On the other hand, in the case of a synthetic fiber, the following aspects are possible in addition to the aforementioned aspects (of course, a combination with (1) or (2) is possible).
(3) dispersion in a fiber substrate by incorporation.

Furthermore, a material for a fiber to which the present invention is applicable is not particularly limited but examples are as follows (regarding a synthetic fiber, in order to specify a material for a fiber substrate, a commercially available fiber material is exemplified. Therefore, it dose not mean naturally that a fiber of the present invention which is complexed with an antibacterial property imparting glass composition is sold under these trade names):
① natural fiber
　plant fiber: flax, pine apple fiber and the like
　animal fiber: wool, animal hair (mohair, alpaca, kashmir and the like), silk and the like
② synthetic fiber
　regenerated fiber: rayon, tensel, chitin, collagen fiber and the like
　semi-regenerated fiber: acetate, triacetate and the like
　synthetic fiber: polyamide fiber (trade name: Nylon, Amilan, Glilon and the like)
　polyester fiber (trade name: Delrin, Declon, Tetron, Ester, Siluk and the like)
　polyacryl fiber (trade name: Oron, Creslan, Exsran, Bonnel, Acrylan, Kanekaron, Kashimiron, Trelon, Silbaron, Fainel and the like)
　polyvinylalcohol fiber (trade name: Vinylon and the like)
　polyolefine fiber (trade name: Pyren, Melaclon (polypropylene system), Pyren E (polyethylene) and the like)
　polyurethane (Spandex) system fiber (trade name: Likla, Pyren, Spandel, Espa, Oberon, Neolon and the like)

In addition, it is effective to constitute a fiber substrate itself with a heat-resistant fiber such as metha system aramid (trade name: Cornex, Normex and the like), para system aramid (trade name: Kevlar 29, Technola and the like), polybenzimidazole (trade name: PBI and the like), polyamideimide (trade name: KERMEL and the like), carbonized (trade name: Pyromex and the like) or novoloid (trade name: Kainol and the like) for improving antibacterial property. Inter alia, regarding synthetic fibers of polyester, polyamide (for example, nylon system), acrylandpolypropylene, particularlyhigh antibacterial property and high durable antibacterial property are exerted.

In addition, the aforementioned antibacterial fiber can be twisted in a linear manner into an antibacterial twisted yarn. Further, the aforementioned antibacterial fiber can be also constituted as a woven fabric or a non-woven fabric into an antibacterial cloth (final fiber product). Such the antibacterial fiber, antibacterial twisted yarn or an antibacterial cloth can be applied to various clothings of special use such as waterproof clothing in addition to general clothings. As the clothing, there are garment, footwear and caps. Further, in addition to clothings, they can be used, without limitation, in the field for which antibacterial property is required, such as bedding such as towel, blanket, futon, bed linen and the like, wrapping material such as rope, tent, sunshade, sail, bag and the like, mat, interior member for construction (screen, mosquito net, tablecloth, curtain, wall cloth, carpet, flooring, rug, linoleum and the like), or interior member for vehicle such as car, railway rolling stock, ship, aircraft and the like (for example, wall cloth, flooring, carpet, rug, linoleum and the like).

DESCRIPTION OF THE PREFERRED EMBODIMENTS

Embodiments of the present invention are explained by referring to Examples shown in drawings.

Figure 1B:
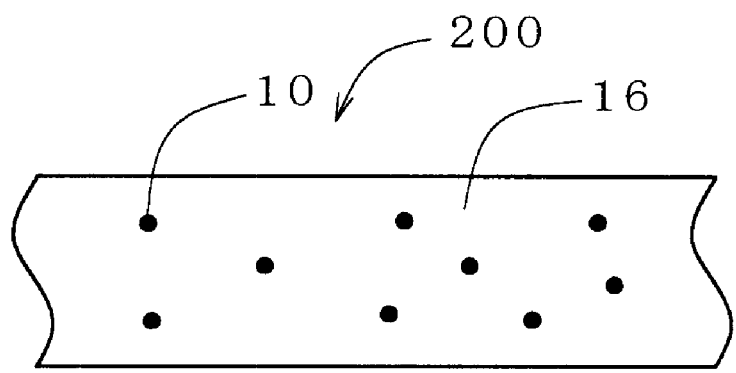

FIGS. 1A and 1B are expanded schematic views for explaining the outline of an antibacterial fiber of the present invention. In an antibacterial fiber 200 shown in FIG. 1A and 1B, an antibacterial property imparting glass composition 10 in the form of, for example, a particle is complexed with a fiber substrate 16 and, as an aspect of complexation, the composition may be fixed on the surface of a fiber substrate 16 ((a): hereinafter, referred to as fixation aspect), or may be dispersed in a fiber substrate 16 ((b): hereinafter, referred to as dispersion aspect). In addition, a dispersion aspect and a fixation aspect can be combined.

In an antibacterial property imparting glass composition 10 of the present Example, $Ag_2O$ is contained, at an amount of 0.1–5.0% by weight, in a glass composition containing 45–67 mol % of $P_2O_5$, 5–20 mol % of $Al_2O_3$, 1–40 mol % of 1, 2 or more selected from MgO, CaO and ZnO, 1–15 mol % of 1, 2 or more selected from $Li_2O$, $Na_2O$ and $K_2O$, and 20 mol % or less of $B_2O_3$. Furthermore, an antibacterial property imparting glass composition 10 of the present Example is prepared into a particle and an average diameter thereof is about 0.05–55 $\mu$m. In addition, such the antibacterial property imparting glass composition 10 is complexed with a fiber substrate 16, for example, at a proportion of 0.1–5.0% by weight.

Figure 2:
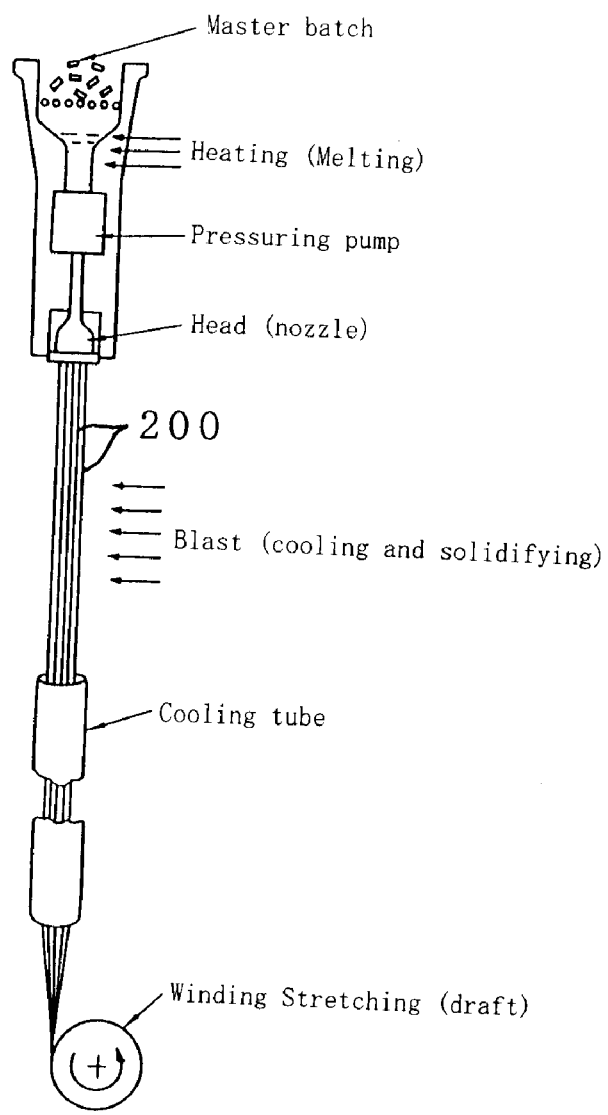
FIG. 2 is a view schematically showing one example of a spinning method for manufacturing an antibacterial fiber of the present invention.

As an aspect of the aforementioned complexation, a dispersion aspect is effective especially when a particle is complexed with a chemical fiber. That is, a particle is incorporated into a spinning dope to become a fiber substrate 16, which can be spun to easily obtain a fiber in the dispersion aspect. FIG. 2 shows one example of a melt spinning method which is effective when a fiber substrate 16 is a thermoplastic polymer material (nylon (polyamide), polyester, polyethylene, polypropylene and the like). That is, a master batch (transient molded material) for a fiber material is melt to make a dope for melt spinning, which is extruded in a cooling medium such as air, water or the like and cooled to solidify into a fiber form.

Figure 3A:
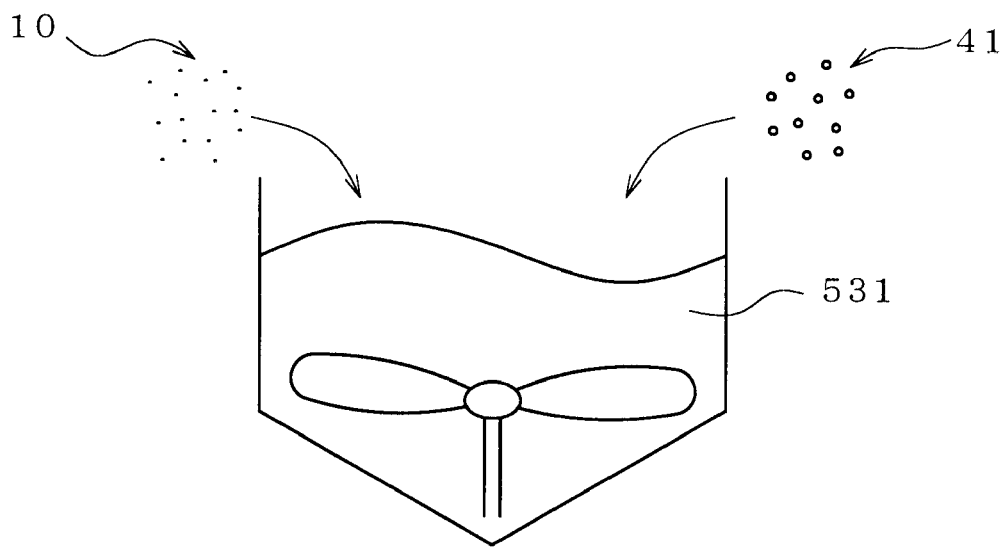
FIGS. 3A to 3D are views schematically showing an example of a method for manufacturing a master batch together with various morphologies of a master batch particle.
Figure 3B:
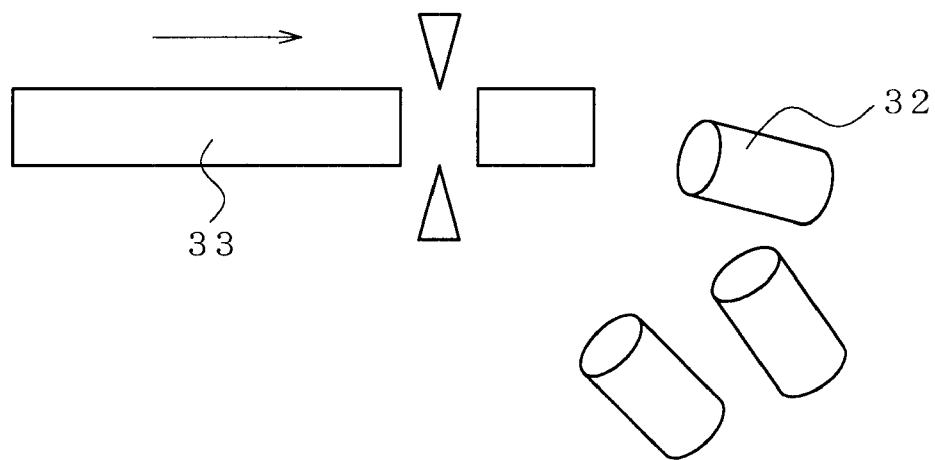
Figure 3C:
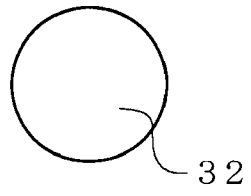
Figure 3D:
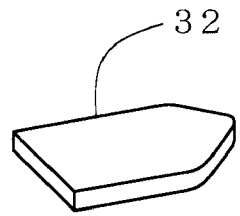

A master batch for spinning can be prepared, for example, as follows: That is, as shown in FIG. 3A, the antibacterial property imparting glass composition 10 as described above is incorporated and blended into a polymer material 41 (a thermoplastic resin is used in this Example) to become a substrate, alone or together with an another antibacterial agent, a filler, a coloring agent such as a pigment and a dye, a dispersant or the like, to obtain a compound 531. The compound 531 can be molded into a particulate form such as a pellet to obtain a master batch particle 32. The master batch particle 32 has a diameter size of around 0.1–10 mm (for example, around 1–4 mm) as a dimension obtained by spherical converting calculation). The shape thereof is not particularly limited but, for example, a particle having the post-like form (for example, cylindrical form) can be obtained by extruding a softened compound in the form of a strand, which is cut into the predetermined length, as shown in FIG. 3B. FIGS. 3C and 3D show an another example of a master batch particle 32, and the former shows a spherical form (for example, it can be prepared by molding and the like) and the latter shows a flake (for example, it can be prepared by crushing and size-adjusting a sheet), being not limiting.

Figure 4A:
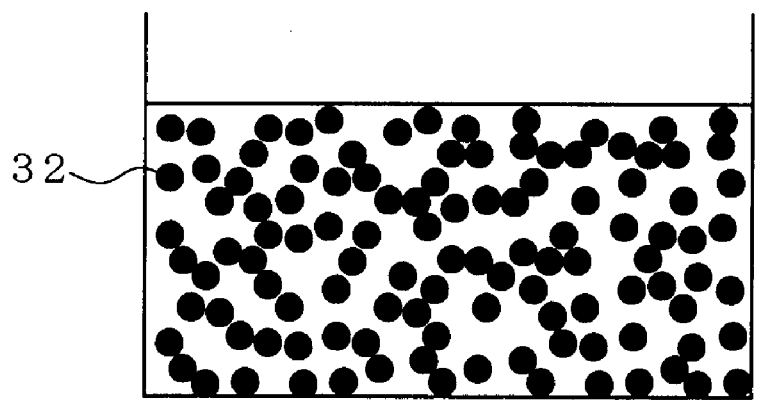
FIGS. 4A and 4B are illustrations showing several aspects of using a master batch.
Figure 4B:
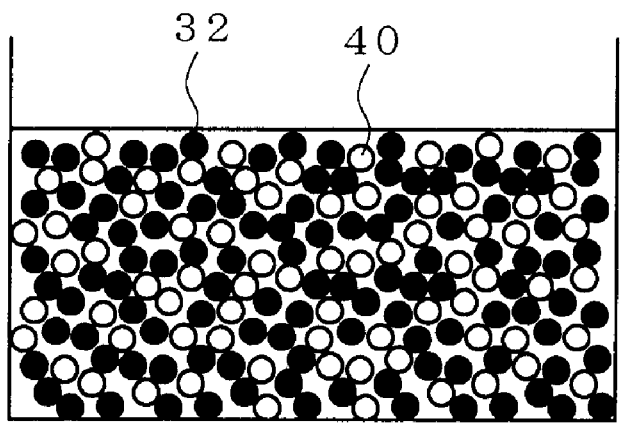

In addition, although a master batch 32 may be used alone for spinning as shown in FIG. 4A, a fiber having the small content of a composite particle than that of a master batch 32 may be prepared by incorporating a suitable amount of a diluting polymer material particle 40 comprising the same or different material of a polymer substrate of a master batch 32 as FIG. 4B. In this case, the content of a composite particle in a fiber is determined by a ratio of a composite particle in a master batch 32 and a ratio of incorporated diluent polymer material particle 40 relative to a master batch particle 32.

Figure 5A:
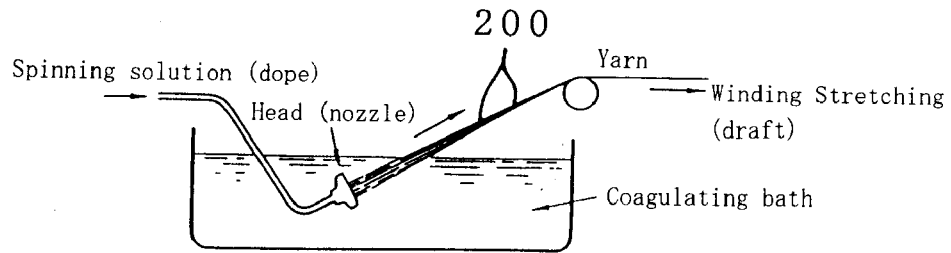
FIGS. 5A to 5C are views schematically showing modified examples of a spinning method for manufacturing an antibacterial fiber of the present invention.
Figure 5B:
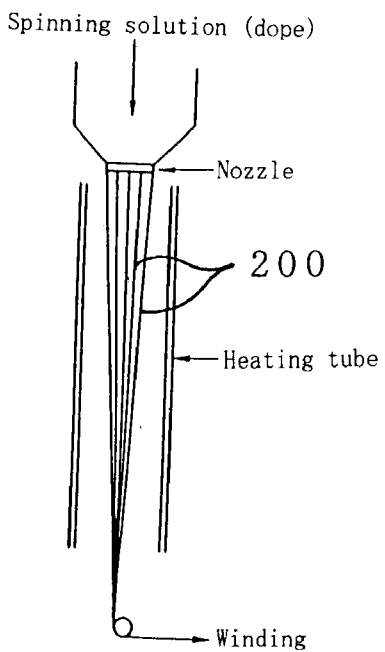
Figure 5C:
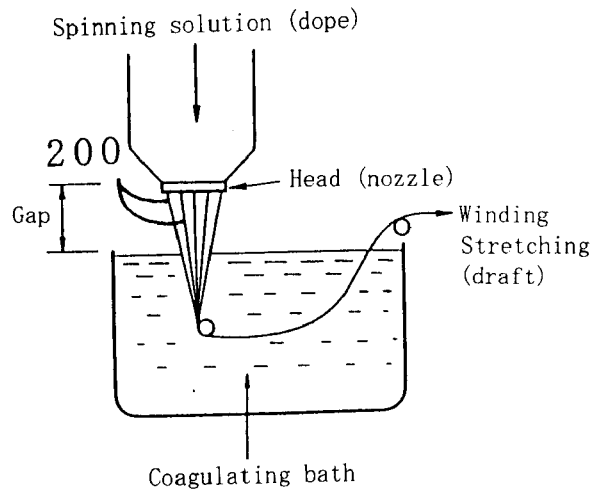

On the other hand, FIGS. 5A to 5C show some other examples of a spinning method. FIG. 5A shows one example of a wet-spinning method and this is a method of dissolving or dispersing a raw material in a solvent to make a spinning solution which is extruded into a coagulating bath through a nozzle and regenerated into a fiber form while removing the solvent. This method is effective in the case where a fiber substrate is, for example, rayon or acryl or vinylon or the like. FIG. 5B shows one example of a dry spinning method and this is a method of extruding the same spinning solution as that of a wet spinning method in a heated gas (air or the like) and evaporating a solvent to regenerate into a fiber form. This method is effective in the case where a fiber substrate is, for example, acetate, vinylon or polyether urethane and the like. FIG. 5C shows one example of a dry and wet spinning method and this is a method of passing a spinning solution through a gap filled with an air to control the oriented state of a molecular chain and removing a solvent in a liquid bath to regenerate into a fiber.

Figure 6A:
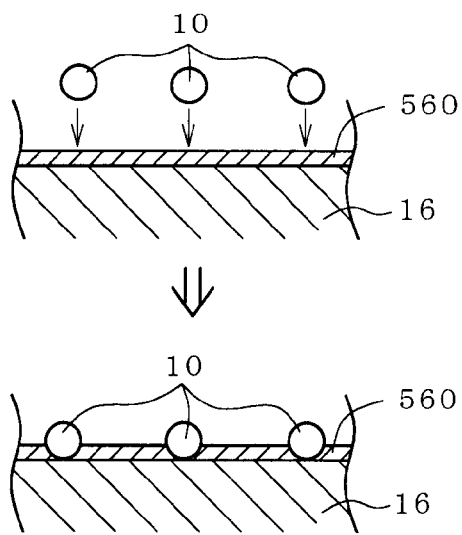
FIGS. 6A to 6C are illustrations for explaining a step for exemplifying several methods of fixing an antibacterial property imparting composite particle on the surface of a fiber substrate.
Figure 6C:
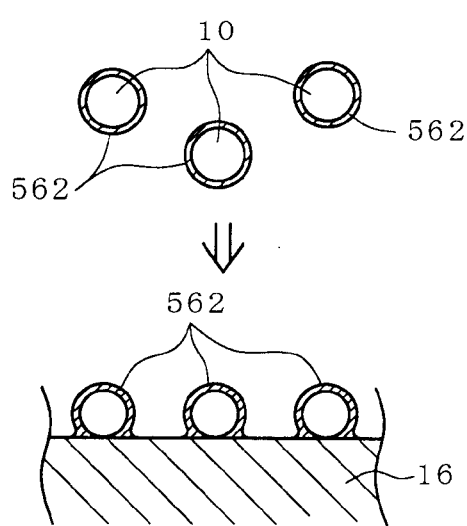
Figure 6B:
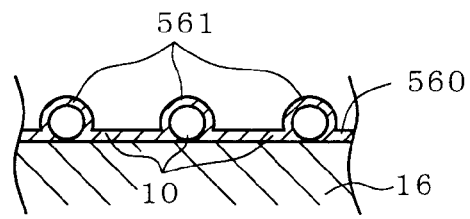

Next, an aspect of fixing an antibacterial property imparting glass composition (glass particle) 10 on the surface of a fiber substrate 16 will be explained. This complexing method is particularly effective in the case where a natural fiber or the like is used as a fiber substrate. FIGS. 6A to 6C show some examples thereof. FIG. 6A shows an example in which a glass particle 10 is fixed as an adhesive form via an adhesive polymer layer 560 formed on the surface of a fiber substrate 16. In addition, as shown in FIG. 6B, the surface of a fixed glass particle 10 may be covered with an overcoat 561 composed of a polymer or the like. FIG. 6C is an example in which the surface of a glass particle 10 is pre-covered with a fixing resin layer 562 and the fixing resin layer is adhered to the surface of a fiber substrate 16 while softening it by heating and, thereafter, the resin layer is cured to fix a composite particle 10.

Figure 7A:
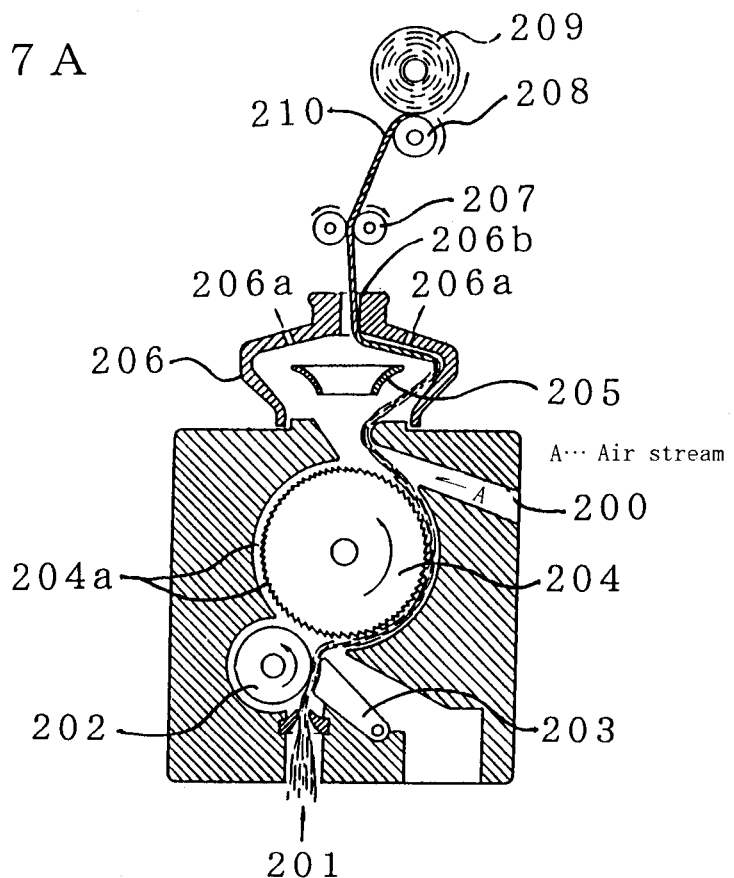
FIGS. 7A to 7D are cross-sectional views showing one example of an air twisting machine for manufacturing an antibacterial twisted yarn of the present invention and a view showing a variety of morphologies of an antibacterial twisted yarn.

The fiber obtained as described above can be processed into a twisted yarn via a spinning step and, thereby, an antibacterial twisted yarn of the present invention can be obtained. Although a variety of known methods can be adopted as a twisting method, FIG. 7A shows an air twisting machine which is one example of a spinning machine therefor. The outline for operations is as follows: A fiber bundle 201 is fed between a supply roller 202 and a forcible member 203. The forcible member 203 puts a fiber bundle 201 between itself and the supply roller 202 by forcing by a spring not shown. By rotating the supply roller 202 at this state, the fiber bundle 201 is conveyed to a combing roller 204. The outer circumference of the combing roller 204 is provided with graved teeth of a saw-like knife 204a, which scrapes the fiber bundle 201 with a tip of tooth 204a by its rotation. Thereby, the fiber bundle 201 is fed into a rotor 206 while being separating into individual fibers by centrifugal force of rotation of a combing roller 204 and by a stream of an air introduced through an air passage 200. In addition, a symbol 205 is a separator for distributing an air stream.

The rotor 206 is for twisting the fiber bundle 201. For example, it rotates at a high speed at around 30000 rpm and a plurality of discharge holes 206a are provided on the circumference of a thread guiding tube 206b at a constant interval and an air introduced through the air passage 200 is discharged therethrough. Thereby, a row of separated fibers sucked into a thread guiding tube 206b off a tooth tip of a combing roller 204 undergoes an action by centrifugal force of high rotation of a rotor 206 and by a stream of an air and, thus, is blown onto an inner wall of a rotor 206 while swirling along a rotating axial line. At this point, when a seed thread is hanged down from the thread guiding tube 206b, a fiber row blown on an inner wall of a rotor 206 is twisted by rotation of the rotor 206 to give a twisted yarn 210. A twisted yarn 210 is drawn out with a pinch roller 207 and wound on a cheese 209 by rotation of a roller 208.

Figures 7B, 7C, 7D:
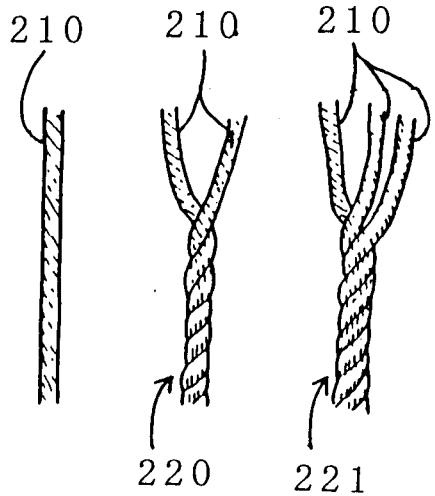
Figure 8:
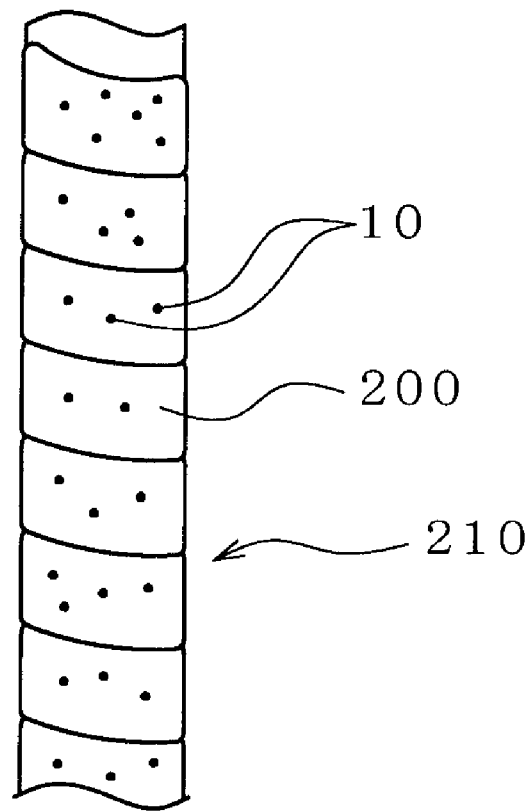
FIG. 8 is a view schematically showing a single yarn which is constituted as an antibacterial twisted yarn of the present invention.

FIG. 7B shows one example of a single yarn 210 thus prepared. As shown conceptionally in FIG. 8, the single yarn 210 has the structure in which, in individual fibers 200, a glass particle 10 is dispersed in its fiber substrate or the particle is fixed on the surface of a substrate. In addition, as shown in FIGS. 7A to 7D, a plurality of the above single yarns may be twisted to make a doubled yarn. FIG. 7C is an example of a twin yarn 220 obtained by twisting two such the single yarns and FIG. 7D shows an example of a three yarned yarn 221 obtained by three yarns. FIGS. 7A to 7D and FIG. 8 only show a part of embodiments of a twisted yarn using an antibacterial fiber of the present invention. It goes without saying that a variety of modifications may be done, for example, a plurality kinds of fibers of different substrates may be twisted to give a blended yarn or a plurality of twisted yarns may be twisted to give a twisted blended yarn. In addition, in a blended yarn or a twisted blended yarn, the content of a particle and distribution aspect in a twisted yarn may be adjusted by substituting a part of a fiber (single yarn) to be twisted with a normal fiber (single yarn) which is not to be complexed with an antibacterial property imparting glass composition 10.

In addition, in an antibacterial twisted yarn of the present invention, a fiber is twisted to give a twisted yarn and, thereafter, an antibacterial property imparting glass composition 10 may be fixed on its surface. In this case, as a fiber to be used, a fiber complexed with the above particle may be used, or a non-complexed fiber may be used. In the case of the latter, although a fiber at a stage prior to twisting is not complexed with an antibacterial property imparting glass composition 10, a glass particle 10 is complexed with a fiber as a surface fixed form in a final twisted yarn. Accordingly, it is clear that, from a viewpoint of a fiber alone, it satisfies the requirements of an antibacterial fiber of the present invention and a twisted yarn itself has the structure in which antibacterial fibers of the present invention are twisted.

Figure 9A:
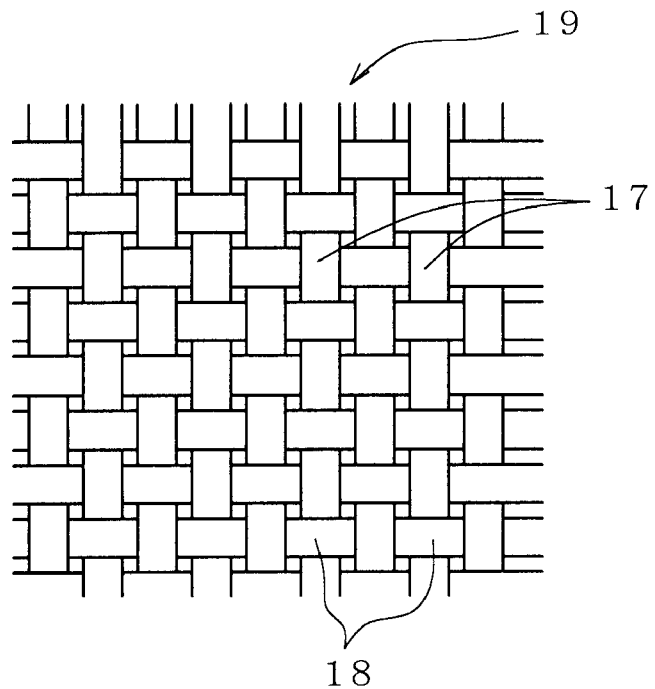
FIGS. 9A to 9C are illustrations showing an example of an antibacterial cloth of the present invention as a woven cloth.

Next, by weaving antibacterial fibers of the present invention, an antibacterial woven fabric which is one aspect of an antibacterial cloth of the present invention can be obtained. FIG. 9A shows an antibacterial cloth 19 in which the above antibacterial fiber of the present invention is used as a warp 18 and a weft 17. Also in this case, an antibacterial property imparting glass composition 10 may be fixed on the surface of a fiber substrate of a twisted yarn as shown in FIG. 9B and may be dispersed in the interior of a fiber substrate as shown in FIG. 9C.

Alternatively, after a twisted yarn is woven, a glass particle 10 may be fixed on the surface thereof. In this case, it is naturally possible that two or more of (A) complexation of a glass particle 10 at a fiber stage (fixation to the surface of a fiber and/or dispersion in a substrate), (B) complexation of a glass particle 10 at a twisted yarn stage (fixation to the surface of a twisted yarn), and (C) complexation of a glass particle 10 at a woven fabric stage (fixation to the surface of a woven cloth) are successively performed. In addition, when twisting is performed after a glass particle 10 is fixed on the surface of a fiber stage and the twisted yarn is used to constitute a woven cloth (that is, when (A) dispersion in a substrate is performed alone), a glass particle 10 is not dispersed in a substrate of a twisted yarn, but a glass particle 10 intervenes between fibers which constitute a twisted yarn. On the other hand, when a glass particle 10 is fixed only at a woven cloth (that is, when (C) is performed alone), a glass particle 10 dose not intervene between fibers which constitute a twisted yarn.

Figure 9B:
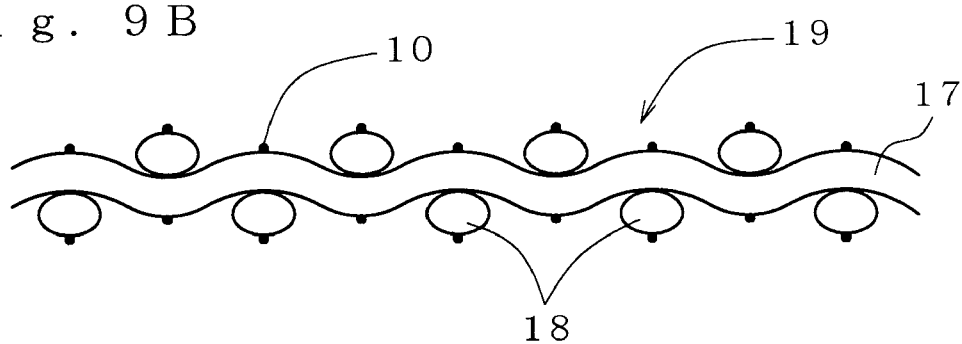
Figure 9C:
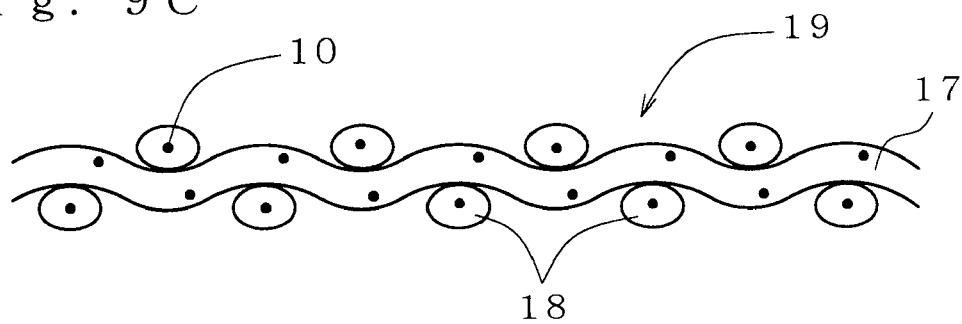
Figure 10:
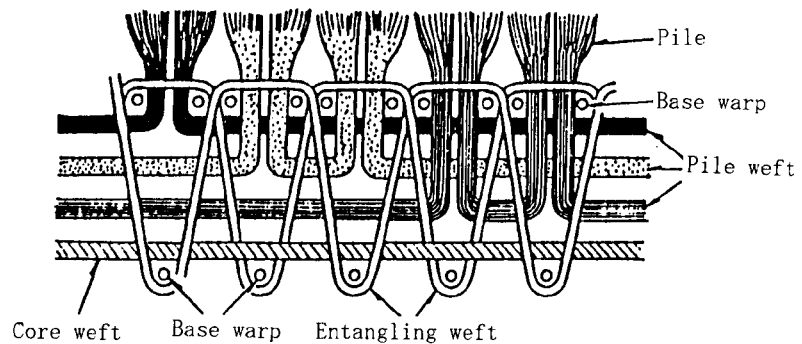
FIGS. 10A and 10B is a cross-sectional view schematically showing several examples in which a woven cloth is constituted as a pile woven fabric.
Figure 10:
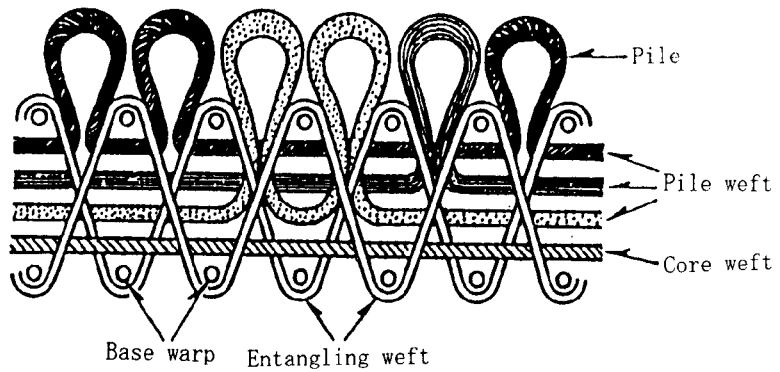

The texture of a woven cloth shown in FIGS. 9A to 9C denotes that of so called plain weave but, naturally, it goes without saying that the woven fabric texture is not limited it. It is of course natural that a variety of variations may be added, such as twill, satin weave, and a combination of two or more of these three textures. In addition, it is possible that a woven fabric of double wefts or double warps is made and a part of the warp or the weft is cut at a suitable position to represent a nap on the surface of a woven fabric, or a weft is floated regularly in a ring shape to make a pile woven fabric having rings. For example, FIGS. 10A and 10B show one example of a cross-sectional texture of a carpet which is application of a pile woven fabric. A pile weft and a core weft are woven with a base warp and tightly bundled and integrated in a thickness direction using an entangling weft. A pile weft is intermittently protruded from the surface of a woven fabric to form a pile and each of proximal ends of the piles are clamped and held by an entangling weft. In the cut pile texture of FIG. 10A, each pile is cut and opened to form a nap and, in a non-cut pile texture of FIG. 10B, each pile is not cut and opened to form a loop.

At least a part of a weft and a warp which constitute a woven cloth can be substituted with the aforementioned blended yarn to constitute a blended woven cloth, or at least a part of a weft and a warp can be substituted with a doubled yarn, or different yarns are used for a weft and a warp (for example, one of them is an antibacterial twisted yarn), or a different fiber is partially incorporated in a stripe manner in a weft or a warp to weave to give a mixed woven fabric.

Figure 11A:
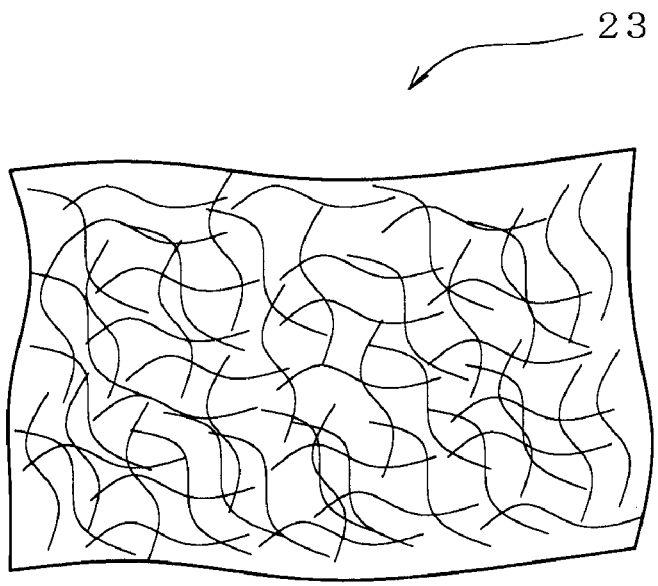
FIGS. 11A to 11C are illustrations showing an example in which an antibacterial cloth of the present invention is constituted as a non-woven fabric.
Figure 11B:
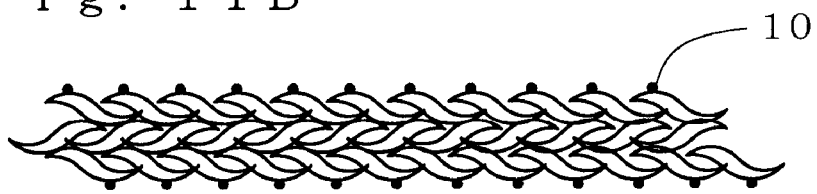
Figure 11C:
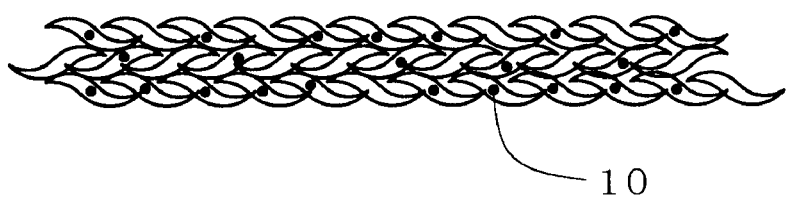

In addition, it is possible that an antibacterial cloth of the present invention may be prepared into a non-woven fabric in which short fibers are randomly laminated and incorporated. FIGS. 11A to 11C show one example of such the antibacterial non-woven fabric 23 schematically. When short fibers are used as an antibacterial fiber of the present invention, the resulting non-woven fabric 23 is an antibacterial non-woven fabric as it is. For example, when a fiber substrate in which an antibacterial property imparting glass composition 10 is dispersed is used, a cross-sectional texture is exhibited as shown in FIG. 11C. When a substrate having the surface with a glass particle 10 fixed thereto is used and/or after manufactured into a cloth in a non-woven form, a glass particle 10 is fixed on the surface of the cloth, the cross-sectional texture is exhibited as in FIG. 11B. In addition, as in a normal non-woven fabric, fibers may be adhered with an adhesive or melt adhered.

Further, in addition to a non-woven fabric, as a form in which an antibacterial fiber of the present invention is directly utilized, there is cottons in which the antibacterial fibers are accumulated in an irregular manner, which may be applied to an antibacterial futon. In this case, a cotton fiber to which an antibacterial property imparting composite particle or an antibacterial property imparting particle alone is fixed may be used and, additionally, a fiber of other material to which the particle is fixed or a substrate in which the particle is dispersed may be used.

EXAMPLES $P_2O_5$, $B_2O_3$, $Al_2O_3$, MgO, CaO, ZnO, $Li_2O$, $Na_2O$, $K_2O$ and $SiO_2$ were mixed so that each has a ratio (mol %) shown in Table 1, and $Ag_2O$ was mixed therein at a ratio by weight shown (% by weight) in Table 1, which was melt in an electric furnace at 1300–1400° C. for 1 hour. Thereafter, a melt was removed from an electric furnace and flown out on a carbon plate to cool naturally. After allowing to cool, the glass was finely-divided so that an average particle diameter to be about 2 µm using a roll crusher or a ball mill to obtain an antibacterial property imparting glass composition belonging to the present invention (samples A–H) and samples I–K as a Comparative Example.

TABLE 1

|  | A | B | C | D | E | F | G | H | I | J | K |
|---|---|---|---|---|---|---|---|---|---|---|---|
| $P_2O_5$ (mol %) | 55 | 55 | 48 | 58 | 58 | 52 | 55 | 50 | 70 | 55 | 47 |
| $B_2O_3$ (mol %) | 15 | 15 | 8 | 10 | 15 | 2 | 18 | 15 | 5 | 15 | 3 |
| $Al_2O_3$ (mol %) | 10 | 12 | 12 | 12 | 15 | 15 | 7 | 8 | 12 | 10 | 5 |
| MgO (mol %) | 15 | 5 | — | — | 3 | 20 | 10 | 6 | — | 15 | 15 |
| GaO (mol %) | — | 5 | 5 | — | 3 | — | — | 6 | — | — | — |
| ZnO (mol %) | 5 | 5 | 15 | 10 | 6 | — | 10 | 6 | 10 | 5 | 25 |
| $Li_2O$ (mol %) | — | — | — | 1 | — | — | — | 2 | — | — | — |
| $Na_2O$ (mol %) | — | 3 | 6 | 8 | — | 3 | — | 2 | 3 | — | 0 |
| $K_2O$ (mol %) | — | — | 6 | — | — | 4 | — | — | — | — | 5 |

TABLE 1-continued

|  | A | B | C | D | E | F | G | H | I | J | K |
|---|---|---|---|---|---|---|---|---|---|---|---|
| SiO$_2$ (mol %) | — | — | — | 1 | — | 4 | — | 5 | — | — | — |
| Ag$_2$O (wt %) | 2 | 2.5 | 1.2 | 2 | 2 | 1.5 | 3 | 1.8 | 2.5 | 4.5 | 2 |

A master batch containing the resulting respective samples A–K at 20% by weight relative to a polyester resin for a fiber (transient molded product) was made, the master batch and a polyester for a fiber are blended so that the content of each of samples A–K is 1% by weight, which was spun and stretched to make an antibacterial fiber of about 2 denier. Then, this fiber was used to make an antibacterial cloth (woven fabric) according to the aforementioned method, to obtain woven fabric samples for an antibacterial test (Examples 1–8 belonging to the present invention, and Comparative Examples 1–3 (see Table 2)).

Regarding the above respective samples for an antibacterial test, as a resistance to light discoloration test, extents of discoloration of samples in a woven fabric form for an antibacterial test was measured by spectrometer as color difference (ΔE)' after they were irradiated with a xenon lamp 450 W/m$^2$ for 200 hours. In a resistance to discoloration test, discoloration evaluation was performed by measuring color difference (ΔE), wherein 1 or less was ○ and above 1 is ×.

Further, at a point when woven samples for an antibacterial test were immersed into an acidic solution having the hydrogen ion concentration of about 4 at 130° C. for 90 minutes and, thereafter, immersed into a distilled water at 25° C. for 24 hours, an amount of Ag which dissolved out from woven fabric samples for an antibacterial test was evaluated. An evaluation was performed as follows: An amount of dissolution out of 300 ng/g/day or more is ○ and that below 300 ng/g/day is ×. In addition, at a point when woven samples for an antibacterial test were immersed into an alkaline solution having the hydrogen ion concentration of about 13 at 100° C. for 50 minutes and, thereafter, immersed into distilled water at 25° C. for 24 hours, an amount of Ag which dissolved out from woven fabric samples for an antibacterial test was evaluated in the same way as the above acidic solution, wherein an amount of dissolution out of 300 ng/g/day or more is ○ and that below 300 ng/g/day is ×.

The results of each test are shown in Table 2.

TABLE 2

|  | Example 1 | Example 2 | Example 3 | Example 4 | Example 5 | Example 6 | Example 7 | Example 8 | Comparative example 1 | Comparative example 2 | Comparative example 3 |
|---|---|---|---|---|---|---|---|---|---|---|---|
| Glass-containing sample | A | B | C | D | E | F | G | H | I | I | K |
| Discoloration evaluation | ○ | ○ | ○ | ○ | ○ | ○ | ○ | ○ | ○ | × | ○ |
| Resistance to acidic solution test | ○ | ○ | ○ | ○ | ○ | ○ | ○ | ○ | × | ○ | × |
| Resistance to alkaline solution test | ○ | ○ | ○ | ○ | ○ | ○ | ○ | ○ | × | ○ | × |
| Antibacterial evaluation after resistance to acidic solution test | ○ | ○ | ○ | ○ | ○ | ○ | ○ | ○ | × | ○ | × |
| Antibacterial evaluation after resistance to alkaline solution test | ○ | ○ | ○ | ○ | ○ | ○ | ○ | ○ | × | ○ | × |

Woven fabrics samples 1–8 for an antibacterial test complexed with samples A–H (see Table 1) showed the excellent results in all of resistance to light discoloration, resistance to acidic solution test, and resistance to alkaline solution test. Regarding Examples 1, 5 and 7 containing samples A, E and G (see Table 1) containing neither of Li$_2$O, Na$_2$O and K$_2$O, the excellent results were shown in all of resistance to light discoloration test, resistance to acidic solution test, and resistance to alkaline solution test. In addition, for example, with respect to an amount of Ag dissolved out in a resistance to acidic solution test and that in a resistance to alkaline solution test of a woven cloth sample for an antibacterial test in Example 1, the amount was 800 ng/g/day in a resistance to acidic solution test, and the amount was 1000 ng/g/day in a resistance to alkaline solution test. An amount of Ag dissolved out in Examples 1–8 was 300–2000 ng/g/day in a resistance to acidic solution test and 320–2500 ng/g/day in a resistance to alkaline solution test.

On the other hand, since a sample I (see Table 1) containing a large amount of P$_2$O$_5$ (70 mol %) was used in Comparative Example 1 which does not belong to the present invention, the solubility of the sample (glass composition) was too large, an amount of Ag dissolved out was shown to be 200 ng/g/day in a resistance to acidic solution test and the amount of Ag was shown to be 270 ng/g/day in a resistance to alkaline solution test. In addition, since a sample J (see Table 1) containing a large amount of $Ag_2O$ (5.5% by weight) was used in Comparative Example 2, color difference (ΔE) was 1 or more in a resistance to light discoloration test due to the influence of $Ag_2O$ having high discoloring property.

Since a sample K (see Table 1) containing a large amount of MgO and ZnO (43 mol %) in Comparative Example 3, resistance to water, resistance to acid and resistance to alkali of a woven fabric for an antibacterial test were lowered. Regarding an amount of Ag dissolved out in a resistance to acidic solution test and that in a resistance to alkaline solution test in this Comparative Example 3, the amount was 100 ng/g/day in a resistance to acid test and the amount was 210 ng/g/day in a resistance to alkali test.

Furthermore, an antibacterial test was carried out on each sample of the aforementioned antibacterial test after a resistance to acidic solution test and a resistance to alkaline solution test based on the unified test procedures prescribed by a conference for evaluating new function of a fiber product. That is, 1/50 normal bouillon containing $10^5$ cells of *Staphylococcus aureus* was added dropwise to each sample for an antibacterial test (Examples and Comparative Examples) according to $JISL1902^{-1998}$ and cultured at 37° C. for 18 hours to calculate the number of living bacteria.

On the other hand, 1/50 normal bouillon containing $10^5$ cells of *Staphylococcus aureus* was added dropwise to a woven-like sample (standard sample) composed of a polyester for a fiber containing no respective samples A–K as an antibacterial agent and cultured at 37° C. for 18 hours to calculate the number of bacteria. Antibacterial evaluation was performed as follows: the number of living bacteria for a standard sample containing no respective samples A–K is X and the number of living bacteria of a sample for an antibacterial test containing respective samples A–K (Examples and Comparative Examples) is Y and, when a value of log (X/Y) is 2.2 or more, it was evaluated as ○ and, when the value was less than 2.2, it was evaluated as ×.

As shown in Table 2, a value of log (X/Y) as antibacterial property after a resistance to acidic solution test and a resistance to alkaline solution test was less than 2.2 in Comparative Examples 1 and 3. This is because a sample I (see Table 1) containing a large amount of $P_2O_5$ (70 mol %) was used in Comparative Example 1 and a sample K (see Table 1) containing a large amount of MgO and ZnO (43 mol %) was used in Comparative Example 3 and, thus, resistance to acid and resistance to alkali of antibacterial property were lowered. In example 1–8, antibacterial durability was high in resistance to acid and resistance to alkali.

Furthermore, samples of respective Examples 1–8 and Comparative Examples 1–3 were subjected to alkali weight loss and staining treatment and the treated samples were subjected to an antibacterial test based on the above-mentioned test procedures. Alkali weight loss treatment was performed according to a bath ratio of 1:50 using a 4% by weight aqueous solution of sodium hydroxide (hydrogen ion concentration; about 13.5) under immersion treatment at 98° C. for 40 minutes.

The staining treatment was performed under immersion treatment at 130° C. and for 60 minutes using a dye containing Miketone Polyester Blue FBL (manufactured by Mitsuikagaku) at 2% by weight/owf. Thereafter, reductive washing was performed at 80° C. for 20 minutes using a washing solution containing 2 g/l of sodium carbonate, 2 g/l of sodium hydrosulfite and 1 g/l of aramidine D.

In an antibacterial test after alkali weight loss or staining treatment, samples in Examples 1–8 showed values of log (X/Y) of 2.2 or more. In addition, samples of Comparative Examples 1–3 showed values of log (X/Y) of less than 2.2. From this, it is seen that samples of Examples belonging to the present invention show high durability regarding antibacterial property to the aforementioned alkali weight loss or staining treatment.

As used herein, "main component" means a component having the largest content unless otherwise indicated.

What is claimed is:

1. An antibacterial property imparting glass composition which comprises:
   0.1 to 5.0% by weight of $Ag_2O$,
   45–67 mol % of $P_2O_5$,
   5–20 mol % of $Al_2O_3$
   20 mol % or less of $B_2O_3$, and
   1–40 mol % of one or more selected from the group consisting of MgO, CaO and ZnO.

2. The antibacterial property imparting glass composition according to claim 1, wherein one or more selected from the group consisting of $Li_2O$, $Na_2O$ and $K_2O$ is contained in the glass composition in an amount of 15 mol % or less.

3. The antibacterial property imparting glass composition according to claim 1, wherein the antibacterial property imparting glass composition is prepared into a particle form and an average particle diameter thereof is 0.05–55 μm.

* * * * *